United States Patent
Lepple-Wienhues (10) Patent No.: US 11,147,440 B2
(45) Date of Patent: Oct. 19, 2021

(54) OTOSCOPE AND OTOSCOPIC METHOD BASED ON SPECTRAL ANALYSIS

(71) Applicant: Helen of Troy Limited, St. Michael (BB)

(72) Inventor: Albrecht Lepple-Wienhues, Pontarlier (FR)

(73) Assignee: Helen of Troy Limited, St. Michael (BB)

( * ) Notice: Subject to any disclaimer, the term of this patent is extended or adjusted under 35 U.S.C. 154(b) by 662 days.

(21) Appl. No.: 15/307,778

(22) PCT Filed: May 5, 2015

(86) PCT No.: PCT/EP2015/000914
§ 371 (c)(1),
(2) Date: Oct. 28, 2016

(87) PCT Pub. No.: WO2015/169435
PCT Pub. Date: Nov. 12, 2015

(65) Prior Publication Data
US 2017/0049309 A1    Feb. 23, 2017

(30) Foreign Application Priority Data

May 5, 2014  (WO) .................. PCT/EP2014/001195

(51) Int. Cl.
*A61B 1/227* (2006.01)
*A61B 1/00* (2006.01)
(Continued)

(52) U.S. Cl.
CPC .......... *A61B 1/227* (2013.01); *A61B 1/00009* (2013.01); *A61B 1/00057* (2013.01);
(Continued)

(58) Field of Classification Search
CPC ......... A61B 1/227; A61B 1/2275; A61B 1/05; A61B 1/00057; A61B 1/00009;
(Continued)

(56) References Cited

U.S. PATENT DOCUMENTS 5,078,150 A * 1/1992 Hara .................... H04N 5/2254
                                                  600/476
6,110,106 A * 8/2000 MacKinnon ......... A61B 5/0071
                                                  600/160
(Continued)

FOREIGN PATENT DOCUMENTS

CN     101984915 A     3/2011
JP     2004535834 A   12/2004
(Continued)

OTHER PUBLICATIONS

International Search Report, dated Jul. 22, 2015, for International Application No. PCT/EP2015/000914, 6 pages.

Primary Examiner — Jessica Weiss
(74) Attorney, Agent, or Firm — Rankin, Hill & Clark LLP (57) ABSTRACT

An otoscope device is disclosed comprising a radiation sensing unit configured for detecting radiation reflected by the patient's outer ear, especially by the eardrum. The otoscope device further comprises electronic and/or optic means configured for determining spectral information of reflected radiation, especially with respect to wavelengths shorter than 500 nm to 480 nm, and configured for determining a ratio of radiation in the spectrum below 480 nm to 500 nm to radiation in the spectrum above 480 nm to 500 nm, especially based on a specific intensity of reflected radiation within the spectrum of blue light and/or UV radiation. Further, a method is disclosed for identifying and/or locating objects in a subject's ear or to a method of identifying or characterizing an eardrum. Still further, a (Continued)

method is disclosed for determining the risk of a pathologic state of the eardrum and its vicinity and to provide the user with a risk index for inflammation.

12 Claims, 4 Drawing Sheets

(51) Int. Cl.
    *A61B 1/05*              (2006.01)
    *A61B 1/06*              (2006.01)
    *A61B 5/00*              (2006.01)
    *A61B 5/12*              (2006.01)

(52) U.S. Cl.
    CPC .............. *A61B 1/05* (2013.01); *A61B 1/0638* (2013.01); *A61B 1/0684* (2013.01); *A61B 5/0075* (2013.01); *A61B 5/0084* (2013.01); *A61B 5/12* (2013.01); *A61B 5/6815* (2013.01); *A61B 5/6817* (2013.01); *A61B 5/6865* (2013.01)

(58) Field of Classification Search
    CPC ... A61B 1/0638; A61B 1/0684; A61B 5/0075; A61B 5/0084; A61B 5/12; A61B 5/6815; A61B 5/6817; A61B 1/0646; A61B 1/06; A61B 1/07; A61B 1/0661; A61B 1/0676; A61B 1/0669
    USPC ........................................................ 600/200
    See application file for complete search history.

(56) References Cited

U.S. PATENT DOCUMENTS

| | | | | |
|---|---|---|---|---|
| 7,058,441 B2 * | 6/2006 | Shahar | ................. | A61B 5/0075 600/475 |
| 8,115,934 B2 * | 2/2012 | Boppart | ............. | G01B 9/02014 356/479 |
| 8,617,061 B2 | 12/2013 | Magalhães Mendes et al. | | |
| 9,392,933 B2 * | 7/2016 | Bedard | ................... | A61B 1/227 600/474 |
| 9,565,996 B2 * | 2/2017 | Berkner | ............. | A61B 1/00186 600/407 |
| 2004/0158157 A1 * | 8/2004 | Jensen | ................... | A61B 5/062 600/476 |
| 2005/0228231 A1 * | 10/2005 | MacKinnon | ....... | A61B 1/00186 600/180 |
| 2006/0282009 A1 * | 12/2006 | Oberg | .................. | A61B 5/0084 600/559 |
| 2011/0026037 A1 | 2/2011 | Forster et al. | | |
| 2013/0289353 A1 | 10/2013 | Seth et al. | | |
| 2014/0012141 A1 * | 1/2014 | Kim | ................... | A61B 1/00048 600/476 |
| 2014/0206979 A1 * | 7/2014 | Berkner | ............. | A61B 1/00186 600/407 |
| 2014/0316238 A1 * | 10/2014 | Berkner | ................ | A61B 1/042 600/407 |
| 2015/0044098 A1 | 2/2015 | Smart et al. | | |
| 2015/0351637 A1 * | 12/2015 | Ruppersberg | ........ | A61B 1/2275 600/474 |
| 2016/0058274 A1 * | 3/2016 | Chiba | ................ | A61B 5/14546 600/328 |
| 2016/0278678 A1 * | 9/2016 | Valdes | ............... | A61B 1/00009 600/476 |

FOREIGN PATENT DOCUMENTS

| | | | | |
|---|---|---|---|---|
| JP | 2006084425 A | 3/2006 | | |
| JP | 2014505494 A | 3/2014 | | |
| JP | 2015530886 A | 10/2015 | | |
| WO | 2007049562 A1 | 5/2007 | | |
| WO | 2009/157825 A1 | 12/2009 | | |
| WO | WO-2009157825 A1 * | 12/2009 | ........... | A61B 1/0607 |
| WO | 2014117954 A2 | 8/2014 | | |
| WO | WO-2014117956 A2 * | 8/2014 | ............... | A61B 5/74 |

* cited by examiner

OTOSCOPE AND OTOSCOPIC METHOD BASED ON SPECTRAL ANALYSIS

BACKGROUND

Technical Field

The present disclosure relates to an otoscope device, especially configured to be used by a layperson, comprising a portion configured to be introduced in an ear canal of a patient's ear; and an electronic imaging unit configured for capturing at least one image of the patient's outer ear, especially of the eardrum, preferably the electronic imaging unit is an optoelectronic analysis unit. The present disclosure also relates to an otoscope device comprising a radiation sensing unit configured for detecting radiation reflected by the patient's outer ear, especially by the eardrum. The present disclosure also relates to a method of identifying and/or locating objects in a subject's ear, comprising the steps: providing an electronic imaging unit; capturing at least one image of the patient's outer ear, especially of the eardrum; determining spectral information to identify objects shown in the at least one image by electronic and/or optic means, especially in order to identify a healthy eardrum. In particular, the present disclosure relates to an otoscope device according to one of the respective independent device claims as well as to a method of identifying and/or locating objects in a subject's ear or to a method of identifying an eardrum according to one of the respective independent method claims.

Looking into ears is called "otoscopy". Otoscopy is a standard medical examination technique established more than 100 years ago. Medical students learn otoscopy early in their studies during the practical course in physiology. Otoscopic examination assists the skilled physician in examining the ear canal or eardrum which may be affected, e.g., by otitis media (OM), otitis media with effusion (OME), otitis externa, and eardrum perforation. OME is defined by the presence of middle ear effusion, i.e., a liquid behind an intact tympanic membrane (eardrum) without signs or symptoms of acute infection. OM and OME belong to the most frequent pediatric diagnoses. Object recognition in otoscopy is also directed to the identification of particles or any material, e.g., hair, earwax, foreign objects, etc., which may obstruct the ear canal in front of the eardrum. Such applications are highly desired for routine care.

For any application of an otoscope or its mode of use, it is desired to allow its user to identify or locate objects within the ear canal or at its end, in particular the eardrum itself or any objects adhering to an inner wall of the ear canal or to the eardrum. In a further step, it may also be desired to characterize an identified object in more detail.

Description of the Related Art

The art of reliably and securely handling an otoscope as well as interpreting otoscopy is currently restricted only to well-trained physicians. It is not amenable to layperson caretakers or assistant staff, e.g., nurses. In particular, with an otoscope of the art, reliable identification of objects within the ear canal may only be carried out by well-trained physicians. The younger the patient the more difficult it is to even visualize the eardrum for a sufficient amount of time to make a diagnosis. A study published in the US as a result of a survey has shown that even physicians often fail to correctly determine the status of e.g., the subject's eardrum or fail to correctly interpret the image provided by the otoscope. Such failures can result in misinterpretation of the status of the inner ear canal or the eardrum. As a consequence, e.g., over-medication with antibiotics for treating supposed inflammations of the eardrum occurs, because physicians tend to err on the side of caution.

The otoscopic methods known in the art are subject to well-trained physicians which are capable of interpreting images captured within the ear canal, especially in order to carry out diagnosis. Depending on the content of the captured images, the physician usually has to adjust the otoscope, such as illumination or a relative position of the otoscope within the ear canal.

Consequently, until today otoscopy has almost exclusively been applied by well-trained medical doctors. However, it would be desirable to provide an otoscope which assists in determining/discerning different objects within the ear canal more reliably, even when handled by laypersons. It would be highly desirable to extend the capability of otoscopy beyond the trained professionals. Due to its broad spectrum of applications, it should be made amenable to any layperson, such as parents, who may desire to, e.g., examine whether objects like hairs, earwax, or other particles are located in the children's ear canal. Also, during childhood, otitis media (OM) or otitis media with effusion (OME) are frequent and often occur repeatedly. Thus, otoscopy should be made amenable to parents who are not skilled at all, at least in order to carry out a kind of pre-diagnosis, or to assess a likelihood of inflammation of the eardrum, or to follow-up an earlier diagnosis. The parents should be provided with information which facilitates their decision if it is required to visit a physician. In case a child is sick, e.g., complains about earache, such an otoscope may allow the parents to better estimate the underlying cause. Any more advanced or final disease diagnosis may/should then be carried out by a specialized physician.

U.S. Pat. No. 8,617,061 B2 describes a device for measuring and analyzing the color of the outer ear and ear canal, wherein a tri-color emitter and a tri-color sensor are provided in conjunction with optical fibers for conducting emitted and reflected light, respectively, wherein emission of light by the emitter is independently controlled in its three components. The tri-color sensor is adapted to an existing otoscope. This invention aims for an objective measurement of red shifted color reflection in case of inflammation in the ear. This invention, however, does not address the aforementioned problem of needing a trained specialist to perform the procedure, nor does it address the challenge of identifying and/or locating the eardrum in order to gain clinical relevant information from that structure.

This invention also fails to obtain spatial information about the spectral properties of reflected light. E.g., reflected light with a red shift collected into a lightguide could originate either from a reddish eardrum or from a reddish ear canal.

It is one object of the present disclosure to provide a device, especially an otoscope, configured for electronically identifying and/or locating objects in a subject's ear in a reliable way, the device/otoscope preferably being provided for use by laypersons without special training. It is a further object of the present disclosure to provide a method of identifying and/or locating objects, especially the eardrum, in a subject's ear in a reliable way. The object may also be described as accurately characterizing a specific object, once the object has been identified and/or located.

BRIEF SUMMARY

In particular, at least one of the above mentioned objects is achieved by an otoscope device, especially configured to be manipulated by a layperson, comprising: a portion configured to be introduced in an ear canal of a patient's ear; and an electronic imaging unit configured for capturing at least one image, especially a color image, of the patient's outer ear, especially of the eardrum, especially based on reflected radiation of radiation emitted by at least one source of radiation, preferably the electronic imaging unit is an optoelectronic analysis unit; wherein the otoscope device further comprises electronic and/or optic means, especially a logic unit, configured for determining spectral information or configured for analysis of the at least one image, especially with respect to wavelengths shorter than 550 nm or 500 nm or 480 nm, and configured for identifying and/or locating objects shown in the at least one image, especially the eardrum, depending on visible blue spectral components and/or UV spectral components, especially a specific intensity of blue spectral components and/or UV spectral components, preferably relating to an amount of spectral components at longer wavelengths, e.g., above 480 nm or 500 nm. Identifying and/or locating objects may be carried out depending on a specific relation of blue and/or UV spectral components to spectral reflective components having wavelengths above 500 nm or 550 nm. The range of 480 nm to 500 nm or even 550 nm is mentioned in order to provide a limit or threshold value to which it may be referred in order to determine a specific intensity of short wavelength components or a specific ratio, especially a blue to red ratio and/or blue to green ratio. The range of 480 nm to 500 nm may be understood as any range which is appropriate for delimiting blue light or UV radiation from radiation having longer wavelengths, e.g., green light (ca. 480 nm to 560 nm), yellow light (ca. 560 nm to 580 nm), orange light (ca. 580 nm to 630 nm) or red light (ca. 630 nm to 790 nm).

The wording "amount of spectral components" preferably refers to a specific portion of spectral components.

The optoelectronic analysis unit may comprise, e.g., a Bayer filter, i.e., a color filter array.

The present invention is based on the finding that identification or localization of an object, especially the eardrum, may be complicated or hampered essentially by two factors, namely excessive radiation (intensity of radiation which is too high) and/or evaluation of reflections without any reference to localization. In fact, because of the ear canal's geometry, reflections captured by an otoscope may originate from a plurality of different sections of the ear, e.g., due to multiple reflections of the same radiation within the ear canal. Referring to blue/UV spectral components may reduce these effects, which allows for facilitating spectral analysis.

Preferably, the electronic and/or optic means of the otoscope device are configured for calculating a ratio between at least two reflected spectral components or spectral ranges, especially by pixelwise division, e.g., of the respective pixel value in the blue image channel over the pixel value in the green or red image channel.

Preferably, the electronic and/or optic means of the otoscope device are configured for determining a ratio of radiation in the spectrum below 480 nm to 500 nm to radiation in the spectrum above 480 nm to 500 nm, especially the ratio of blue to red spectral components of reflected light, the electronic and/or optic means preferably configured for detecting or characterizing the eardrum depending on a specific minimum or maximum ratio. The ratio may allow to identify specific local area sections of an image or reflected radiation.

Depending on the spectral composition of reflected radiation, it may be advantageous to define one or several appropriate (spectral) threshold values for each specific spectral analysis.

For localizing the eardrum it can be advantageous to define a threshold value for the ratio blue/red (e.g., reflected light intensity I at 480 nm/I at 700 nm) or the ratio blue/green.

In case a relatively high amount of blue spectral components can be detected, it may be appropriate defining the threshold value at a relatively short wavelength, e.g., 480 nm, especially in order to ensure high accuracy of evaluation. In case only a relatively small amount of blue spectral components can be detected, it may be appropriate defining the threshold value at a relatively long wavelength, e.g., 500 nm or even 525 nm or 550 nm, in order to be able to determine a ratio of "blue" to red even in case there are hardly any blue or UV spectral components. Also, it in case a relatively high amount of red spectral components are detected, it may be appropriate defining the threshold value at a relatively short wavelength, e.g., 480 nm, especially in order to "squelch" any effect of, e.g., an inflamed section of the eardrum. In case only a relatively small amount of red spectral components is detected, it may be appropriate defining the threshold value at a relatively long wavelength, e.g., 630 nm to 790 nm, in order to be able to determine a ratio of blue to red, especially with respect to specific surface area sections, which may also allow for medically characterizing the eardrum or specific sections of the eardrum. Defining the threshold value at a relatively long wavelength may particularly be advantageous in case the eardrum has already been identified, especially in order to reliably determine a degree of reddishness.

The electronic and/or optic means may be configured for defining a threshold value depending on the spectrum of reflected radiation.

In particular, it may be advantageous defining at least two threshold values, e.g., a first threshold value in the range of 470 nm to 490 nm, especially 480 nm, and a second threshold value in the range of 620 nm to 640 nm, especially 630 nm. Spectral analysis may be carried out based on one or both threshold values. For example, localization of the eardrum may be carried out based on the first threshold value, and characterizing the eardrum may be carried out based on the second threshold value. In particular, it has been found that spectral analysis based on the first threshold value referring to a ratio between blue and green light may allow for identifying and/or locating the eardrum irrespective of any degree of reddishness.

Likewise, it may be advantageous defining at least two ranges of wavelength, e.g., a first range of wavelength referring to blue light, especially 380 nm to 480 nm, and at least one second range of wavelength referring to green light or red light, especially 480 nm to 560 nm or 630 nm to 790 nm. Spectral analysis may be carried out based on one or both ranges of wavelength. For example, localization of the eardrum may be carried out based on a ratio of the intensity intensities of the first range of wavelength to the intensity intensities of a second range of wavelength of 480 nm to 560 nm, and characterizing the eardrum may be carried out based on a ratio of the intensity intensities of the first range of wavelength to the intensities of a second range of wavelength of 480 nm to 560 nm and/or 630 nm to 790 nm. In particular, it has been found that spectral analysis based on a ratio of blue to green may allow for identifying and/or locating the eardrum irrespective of any degree of reddishness. Also, it has been found that varying intensity most notably impacts the degree of reflections within the red spectrum. Therefore, by referring to a ratio of blue to green, any intensity impact may be reduced. E.g., when the semitransparent eardrum is observed at low illumination levels using a white light source, the eardrum may appear dark to blueish. When the intensity of illumination is increased the eardrum may appear reddish because the reflected red light from the mucosal walls behind the eardrum lining the middle ear cavity surpasses the detection threshold.

In particular, the electronic and/or optic means are configured for identifying and/or locating objects depending on a spectral composition of the at least one image or a pixel or a pixel area of the image which exhibits a specific amount of specific spectral components, especially a specific amount of blue spectral components or spectral components having wavelengths shorter than 500 nm, preferably shorter than 480 nm. Preferably, color information, especially with respect to blue colors, is evaluated. Color information may be evaluated within an acquired image and/or with respect to reflected. Spectral information may involve spatially resolved spectral information.

Thereby, evaluation of an image can be carried out in order to accurately identify and/or locate several objects within the ear canal. Also, a condition, especially a medical condition of a specific object may be determined. Preferably, the eardrum is identified. Nonetheless, also, other objects, e.g., tissue confining the ear canal, may be determined, especially indirectly. In case a specific object (i.e., a specific part or section of the captured image) does reflect a small amount of blue light and/or UV radiation when compared to reflection in the green or red spectral range, most likely this object or section of the ear canal does not contain the eardrum area.

The electronic and/or optic means may comprise a logic unit or processing unit configured for determining/identifying and/or locating an object depending on a specific composition of spectral components, especially depending on a specific threshold value of a degree/amount/ratio/percentage of blue spectral components, especially in relation to green or red light intensities of reflected light.

Alternatively, according to a further aspect of the invention, at least one of the above mentioned objectives may be achieved by an otoscope device, especially configured to be manipulated by a layperson during its application, comprising a radiation sensing unit configured for detecting radiation reflected by the patient's outer ear, especially by the eardrum; wherein the otoscope device further comprises electronic and/or optic means configured for determining spectral information of reflected radiation, especially with respect to wavelengths shorter than 500 nm, and configured for determining a ratio of radiation in the spectrum below 480 nm to 500 nm to radiation in the spectrum above 480 nm to 500 nm, especially based on a specific intensity of reflected radiation within the spectrum of blue light and/or UV radiation, especially near visible UV radiation. The otoscope device may further comprise a portion configured to be introduced in an ear canal of a patient's outer ear.

The present invention is based on the finding that the different tissues within the ear canal, especially the eardrum, exhibit very individual tissue properties having individual optical reflection properties. Reflections of light or near visible radiation may be evaluated in order to determine each individual object, especially the eardrum. In other words: Spectral analysis may be carried out not (only) for assessing a specific color, but also for identifying and/or locating different objects, especially for accurately identifying and/or locating the eardrum. Thereby, according to one aspect, also a likelihood of an inflammation of the eardrum or the presence of an effusion behind the eardrum can be determined, especially after locating the eardrum area using reflective spectral properties.

The present invention is also based on the finding that the properties of the tissue of the eardrum can be evaluated in order to reliably identify a healthy eardrum or transparent sections of an inflamed eardrum. It has been found that an eardrum reflects light or invisible radiation having a specific spectral composition which differs from the spectral composition reflected by tissue surrounding the eardrum. In particular, it has been found that visible or near visible radiation reflected by a healthy eardrum exhibits a spectral composition which is substantially characterized by wavelengths in the spectrum of UV radiation or in the spectrum of blue light, i.e., wavelengths which are shorter than 550 nm or 500 nm, especially shorter than 480 nm to 500 nm or even shorter than 450 nm. In contrast, light reflected by tissues surrounding the eardrum, e.g., tissue confining the ear canal, exhibits a spectral composition which is predominantly characterized by wavelengths in the spectrum of red light, i.e., wavelengths which are considerably longer than 500 nm or 550 nm or even 600 nm, especially up to 780 nm. In other words: It has been found that the eardrum exhibits tissue properties which considerably differ from tissue properties of surrounding tissue, and that these differences may be evaluated in order to reliably identify the eardrum, or even in order to medically/clinically characterize the eardrum, i.e., to determine a medical condition of the eardrum.

The present invention is also based on the finding that an eardrum is a relatively thin tissue, having a thickness corresponding to a few layers of cells and fibers only. In certain areas of the eardrum, blood vessels that may provide any reflections in the red spectrum are scarce or not present at all. In particular, the mean thickness is in the range of approximately, e.g., 40 µm, 50 µm or 120 µm in the central region of the eardrum. Further, it has been found that some areas of an eardrum, e.g., the pars tensa, exhibit a very low reflection coefficient of red or green radiation as compared to blue or UV radiation. In contrast, the reflectance of tissues and matter other than the eardrum, especially tissues like skin tissue or matters like earwax, exhibit a different spectral reflection composition, namely a high reflection coefficient of green and/or red spectral components when compared to blue or UV components. Such other tissues may exhibit a higher reflectance for wavelengths longer than ca. 500 nm as compared to a reflectance for wavelengths shorter than ca. 480 nm or 500 nm. Therefore, evaluating blue spectral components and/or UV spectral components within reflected radiation may improve reliable assessment or identification of the eardrum. Further, it has been found that some parts of the eardrum, especially the pars flaccida or the parts attached to the malleus handle, may also reflect preferably in the green/red spectrum. Therefore, spectral analysis of a color image may reveals typical patterns which allow for identifying and locating the eardrum.

The present invention is also based on the concept that the eardrum may be reliably identified based on a completely different spectral response as compared to surrounding tissue. Surrounding tissue provides a spectral reflection mainly characterized by long wavelengths (red light), whereas the tissue of the eardrum provides a spectral reflection mainly characterized by short wavelengths (blue light). In the range/spectrum of visible light (color spectrum), the blue color and the red color are arranged on opposite ends of the spectrum. In other words: the difference in wavelength or ratio of intensity of reflections of these two colors is at a maximum. Therefore, identification of the eardrum based on analysis of spectral components having wavelengths shorter than 500 nm, preferably shorter than 480 nm, as compared to longer wavelengths may be carried out reliably.

Further, it has been found that in case the intensity of illumination is high, reflectance of mucosa lining the middle ear located behind the eardrum may dominate the spectrum of reflected radiation. Mucosa is essentially red in appearance, especially when the intensity of illumination is high. Therefore, especially in order to achieve high evaluation accuracy, the intensity of illumination may be adjusted when performing spectral analysis.

In otoscopes used by trained specialists, the light intensity can be typically adjusted between dark and a certain maximal intensity. Therefore, the illumination intensity is not standardized. The perceived spectral composition of the reflected light may be influenced by the chosen intensity. E.g., when the semi-transparent eardrum is observed at low illumination levels using a white light source, the eardrum may appear dark to blueish. When the intensity of illumination is increased the eardrum may appear reddish because of the reflected red light from the mucosal walls behind the eardrum lining the middle ear cavity.

The present invention is also based on the finding that a radiation (especially light) reflection mechanism within the eardrum differs from reflection mechanisms within tissue surrounding the eardrum. In particular, a major reflection mechanism of the semi-transparent parts of the eardrum is Rayleigh scattering, whereas the predominant reflection mechanism within tissue surrounding the eardrum is Mie scattering. Rayleigh scattering may be caused by molecular components within the optically transparent thin membrane. These components include collagen fibers, organelle and cellular membrane layers, as well as cytoplasmic and extracellular molecules. In contrast, Mie scattering is the predominant scatter due to hemoglobin-packed erythrocytes and opaque cellular and extracellular particles. In mucosa, skin, etc., short wavelengths will be absorbed almost completely, especially due to multiple scattering and light path extension. In other words: It has been found that due to the tissue properties of parts of the eardrum, the spectral composition of radiation reflected by the eardrum differs considerably from the spectral composition of radiation reflected by any other tissue or object/matter within the ear canal, especially in case the spectral composition of the source of illumination contains major components in the spectrum of wavelengths shorter than 500 nm to 480 nm or is adjusted with respect to this spectrum. The present invention is also based on the concept that the eardrum may be reliably identified and/or located based on evaluation of these different reflection mechanisms. Thus, based on analysis of the spectral composition, identification of the eardrum, especially identification of a healthy eardrum, can be carried out in a reliable way, preferably with respect to the spectrum of wavelengths shorter than 500 nm or 480 nm, especially the blue color spectrum of visible radiation (blue light), especially in comparison with the spectrum of wavelengths longer than 500 nm.

The present invention is also based on the finding that in a second step, once the eardrum has been identified and/or located, an inflammation index characterizing the eardrum may be determined from a previously defined area. An assessment of the immediate vicinity of a previously located eardrum area regarding spectral reflection properties is suited to perform a diagnosis. An inflamed eardrum usually exhibits a greater thickness that a healthy eardrum. Blood capillaries are widened and immune system cells are present. Therefore, under these conditions, reflection spectra may shift away from the short wavelengths towards longer wavelengths, and the ratio of reflected radiation changes, e.g., the blue to red ratio decreases. Also, an effusion behind the transparent eardrum is showing typically a color change due to mucus containing immune cells and cell debris. In this context, it has been found that assessment of a likelihood of inflammation may be carried out depending on a specific level of illumination/radiation, in particular based on a minimum level of illumination/radiation, in order to reduce stray light reflected by surrounding tissues. As surrounding tissues usually will reflect red light, reducing the level of illumination/radiation may facilitate determination of red spectral components which are reflected by the eardrum. Reducing the level of illumination/radiation may allow for reliably evaluating a spectral ratio of the eardrum. In particular, only those red spectral components are evaluated which are reflected from the same region from which blue spectral components are reflected. Only those spectral ratios are evaluated which are characterizing the vicinity of the region which exhibits a high ratio of blue spectral components with respect to red spectral components.

The present invention is also based on the finding that in a second or further step, an index for a likelihood of OM or OME may be determined, in order to provide the user with an advice for further consultation by a physician.

Determining spectral information may refer to analysis of reflected radiation, especially bluish or blue radiation, and/or analysis of at least one image, especially bluish or blue spectral components of the image or a ratio of blue to red, once the image has been acquired. The "ratio of blue to red" may likewise refer to a ration of UV spectral components to red components. As an image may be conceived as a spatially resolved measurement of reflected radiation, the present disclosure may refer to spectral analysis of reflected radiation both directly within reflected radiation and within an acquired image.

The expression "otoscope device" preferably has to be understood as any device which may function as an otoscope. The otoscope device is not necessarily provided in the form of a manual otoscope. For example, the otoscope device may be integrated in a medical device comprising several devices or fulfilling several functions.

The expression "light" preferably has to be understood as visible radiation in the range of 380 nm to 780 nm. The expression "radiation" preferably has to be understood as visible or invisible radiation in the range of 10 nm to 780 nm or even 1000 nm, wherein X-radiation preferably is not comprised. The expression "UV radiation" preferably has to be understood as invisible radiation in the range of 10 nm to 380 nm, especially 100 nm to 380 nm. The expression "UV spectral components" preferably has to be understood as any spectral components of radiation in the range of 100 nm to 380 nm, or respective image information. When referring to the ratio blue to red, the red spectral components may also comprise infrared components, i.e., radiation having a wavelength longer than ca. 790 nm.

The composition of the eardrum may be classified in three layers:
1. core of collagenous connective tissue;
2. outer covering of stratified squamous epithelium (SSE);
3. inner covering of simple cuboidal epithelium (SCE), the inner covering facing the middle ear cavity.

It has been found that by spectral analysis, each of these layers may be identified for identifying, characterizing and/ or locating the eardrum, especially as all these layers contain scarce or no blood vessels, except in the pars flaccida and the region of the malleus handle.

According to one embodiment of the invention, an otoscope device, especially configured to be manipulated by a layperson during its application, is provided, the device comprising a radiation sensing unit configured for detecting radiation reflected by the patient's outer ear, especially by the eardrum; wherein the otoscope device further comprises electronic and/or optic means configured for determining spectral information of reflected radiation, especially with respect to wavelengths shorter than 500 nm to 480 nm, and configured for determining a ratio of radiation in the spectrum below 480 nm to 500 nm to radiation in the spectrum above 480 nm to 500 nm, especially based on a specific intensity of reflected radiation within the spectrum of blue light and/or UV radiation. In particular, it has been found that based on a ratio of spectral components, any influence of changing intensity may be considerable reduced or precluded. Therefore, a ratio based analysis may provide for a high degree of reliability. In fact, the intensity of reflected radiation may considerably differ, e.g., depending on curvature or geometry of the ear canal, or depending on the position of the otoscope's head portion within the ear canal. As the color spectrum may be influenced by the intensity of emitted radiation, spectral analysis of reflected radiation may not ensure very reliable/significant results. By referring to a ratio, any intensity impact may be reduced.

According to one embodiment of the invention, the electronic and/or optic means are configured for determining local spectral information with respect to specific sections of the outer ear or of at least one image, especially with respect to specific pixels or pixel area sections of the at least one image. Referring to the exact location of specific reflections allows for exact evaluation and local correlation. In particular, a surface area portion of the eardrum which exhibits specific characteristics may be evaluated.

According to one embodiment of the invention, the otoscope further comprises at least one source of radiation configured for radiating, especially illuminating the ear canal. The source of radiation may be selected specifically with respect to the fact that predominant reflection from most structures within the ear canal will be in the red spectral range. In particular, a wide band light source with a high intensity component at the UV/blue end of the spectrum may be chosen. In particular, it has been found that an illumination with a light bulb, even a halogen bulb, may not be optimal for performing spectral analysis according to the present invention. Rather, a cold white LED with a high blue to red ratio is favorable. By means of a source of radiation configured for emitting a specific spectrum, especially a source of radiation emitting UV radiation and/or blue light, the eardrum may be identified and analyzed more efficiently and more reliably.

Any other source of visible and/or UV light may be suited, as long as the spectral composition of the emitted radiation is predictable at differing intensities and can be adjusted to the requirements described.

The expression "source of radiation" preferably has to be understood as a source emitting (near visible) UV radiation and/or light, or as a source of radiation in conjunction with at least one guide of radiation, e.g., an optical fiber or a fiber which is specifically configured for guiding UV radiation.

A "guide of radiation" preferably has to be understood as any means for guiding radiation, especially UV radiation and/or light, especially blue light, from a first point towards a second point. According to one embodiment, the guide of radiation is a light guide.

According to one embodiment of the invention, the at least one source of radiation is configured for emitting blue light and/or UV radiation, especially in the range of 500 nm to 100 nm, preferably below 480 nm. Such a source of radiation facilitates identification and analysis of the eardrum. According to one option or variant, the at least one source of radiation may be configured for not emitting radiation or light of specific wavelength, e.g., light having wavelengths in the range between 450 nm and 630 nm, or 480 nm and 580 nm. For example, the at least one source of radiation is configured for only emitting radiation having wavelengths shorter than, e.g., 480 nm or 450 nm and longer than, e.g., 580 nm or 630 nm. In other words: The at least one source of radiation is configured for emitting radiation within or below the range of wavelengths of blue light and within or above the range of wavelengths of red light. Such a source of radiation allows for reliably evaluating a ratio of blue to red spectral components, focusing on these spectral components. Thereby, artefacts or sources of error may be minimized.

Since the predominant reflection from most structures within the ear canal will be in the spectral range of red light, a light source with a (relatively) high intensity component at the UV/blue end of the spectral range may be chosen. It has been found that illumination by means of a light bulb, even a halogen bulb, may not be optimal for performing spectral analysis according to the present invention. Such a standard light source may not provide a sufficient amount of short wavelength components especially when operated at low intensities. Rather, a cold white LED with a high blue to red ratio may be preferred.

According to one embodiment of the invention, the at least one source of radiation is a source of radiation with a specific spectral maximum in the spectrum of visible light below 500 nm, preferably below 480 nm, especially an LED or multiple LEDs with a spectral maximum in the spectrum of blue light between 380 nm and 500 nm, especially 420 nm and 480 nm. The LED may be provided in the form of a white (preferably cold white) LED. The light source or LED may be configured for adjusting the spectrum of emitted light and/or for adjusting an intensity of illumination, especially with respect to a specific spectral range. Thereby, red spectra of emitted light can be reduced, and light reflections of red (especially highly vascularized) tissue can be minimized. This allows for evaluating a ratio of blue to red even in case blue spectral components are only very scarce.

According to one embodiment of the invention, the at least one source of radiation is a source of radiation configured for emitting light in the spectrum below 500 nm, preferably below 480 nm with higher or at least the same intensity than light in the spectrum above 580 nm, preferably above 630 nm. This allows for reliable evaluation of a blue to red ratio and/or a blue to green ratio. Identification of the eardrum may be carried out reliably even in case of an inflamed eardrum.

According to one embodiment of the invention, the electronic and/or optic means are configured for adjusting the spectral composition of radiation emitted by the at least one source of radiation. In particular, the electronic and/or optic means may be configured for adjusting the ratio of the red spectrum, e.g., above 600 nm, to the blue spectrum, e.g., below 500 nm. The spectrum may be adjusted especially with respect to a specific wavelength below 550 nm, preferably below 480 nm to 500 nm, in particular with respect to a spectral maximum within the spectrum of 380 nm to 500 nm, especially 420 nm to 480 nm. Preferably, the spectrum is adjusted with respect to at least two spectral ranges, especially with respect to the blue spectral range and with respect to the green and/or red spectral range. Adjusting the spectral composition of emitted radiation may further improve reliability of identification of the eardrum. In particular, a first image may be captured during emission of radiation with a relatively broad spectrum, and a second or further image may be captured during emission of UV radiation or blue light or during radiation of the ear canal with radiation having an intensity maximum in the spectral range of UV and/or blue radiation. These images may be compared or analyzed in conjunction with each other. Also, a first image may be captured at a low intensity, and a second image at a higher intensity of illumination.

According to one embodiment of the invention, the electronic and/or optic means are configured for calibration of the spectral composition of radiation emitted by the at least one source of radiation, and for comparing a determined spectral composition of reflected radiation with the calibrated spectral composition of emitted radiation. Such electronic and/or optic means allow for reliably identifying and/or locating objects, especially the eardrum. In particular, it may be determined accurately which spectral components have been absorbed by tissue/objects within the ear canal, and which spectral components are reflected spectral components. Calibration may also be carried out with respect to brightness or an intensity of radiation.

Accordingly, the present invention may also relate to a method comprising calibrating a spectral sensitivity of the electronic imaging unit and/or calibrating the spectral composition of the at least one source of radiation and/or brightness of the at least one image. Calibration allows for more reliable analysis of the spectral composition of reflected radiation, and thus, more reliable identification of objects. It has been found that in case the light intensity is very high allowing light for passing through a healthy eardrum, which is semitransparent, a considerable amount of light within the red spectrum may be reflected by the tympanic cavity (especially due to illumination of red mucosa confining the middle ear). Thus, calibrating the brightness of the image or calibrating the intensity of emitted radiation enables more accurate evaluation of the (absolute) degree of red channel reflection and its source. In other words, spectral calibration of an imaging sensor in combination with spectral calibration of illumination means allows for more accurate evaluation of the tissue types and conditions.

In particular, with a method comprising calibration, any (actual) varying voltage of any batteries of an otoscope for carrying out the method does not imply or implicate any source of error. According to one option, electronic compensation means may be implemented in order to avoid spectral shift of illumination, wherein such shifts could be caused by, e.g., varying voltage. Also, the electronic and/or optic means may be chosen such that the spectral properties of the electronic and/or optic means are independent of any supply voltage. Using traditional otoscopes including light bulbs, e.g., incandescent halogen bulbs, it is likely that at low voltage, the spectrum of the illumination is shifted towards the red spectrum, i.e., less energy intensive wavelength. Compensation means may be provided in conjunction with the electronic and/or optic means, or compensation means may be part of the electronic and/or optic means. Calibrating the spectral range and/or the intensity of illumination/radiation facilitates absolute spectral analysis. In other words: sensing components may be provided with calibrated color balance.

Calibration can be carried out, e.g., based on feedback illumination control with respect to different objects or different kinds of tissue, once the respective object or tissue has been identified. Thereby, spectral norm curves with respect to different light intensities may provide further data based on which calibration may be carried out.

According to one embodiment of the invention, the electronic and/or optic means are configured for adjusting the intensity of radiation of the at least one source of radiation, especially configured for reducing the intensity of radiation in case the at least one image exhibits a spectral composition which exceeds a specific amount of spectral components having wavelengths longer than 480 nmm to 500 nm or 550 nm, especially of red spectral components, or in case a ratio of blue to red falls below a specific minimum level. As described above, in case the intensity of radiation allows radiation for passing through the eardrum, a considerable amount of radiation within the red spectrum may be reflected by the tympanic cavity. Thus, reducing the intensity/brightness such that most radiation is reflected by the eardrum allows for minimizing reflections of any tissue behind the eardrum. This enables more accurate evaluation of the degree of red channel reflections and its source.

According to one embodiment of the invention, the electronic and/or optic means are configured for adjusting the intensity of radiation of the at least one source of radiation with respect to specific spectral components of emitted light/radiation. The intensity of radiation may be adjusted within the spectrum of, e.g., blue or green light, especially without varying or with minimum change in the intensity of radiation of any other spectral components. For example, the intensity of emitted blue light and/or the intensity of red light may be adjusted, especially without varying the intensity of radiation of any other spectral components. Thereby, the amount of reflected radiation within a specific spectral range, especially the amount of reflected blue light or UV radiation, may be assessed and evaluated under specific conditions, which may increase accuracy and reliability also.

According to one embodiment of the invention, the otoscope device is a manual otoscope configured for manual application, further comprising: a handle portion allowing a layperson to manipulate the otoscope during its application; and a head portion exhibiting a substantially tapering form extending along a longitudinal axis of the head portion, wherein the head portion has a proximal end adjacent to the handle portion and a smaller distal end configured to be introduced in an ear canal of a patient's outer ear. Preferably, the at least one image is captured by an image sensor which is arranged at the distal tip of the head portion. The image can be captured directly by the imaging unit. It is not necessarily required to guide reflected light within any optical fiber in a proximal direction towards a proximal end of the head portion. A guide of radiation, especially a light guide, may be favorable in order to provide an image sensor which may be arranged at a proximal portion of the head portion, i.e., further back in a conical ear funnel, gaining space at the tip of the head portion. Also, a larger sensor having relatively high light sensitivity may be provided. Not least, a cheaper sensor may be provided, and assembly may be easier in conjunction with guides of radiation.

According to one embodiment of the invention, at least one of the at least one source of radiation and/or the electronic imaging unit respectively is arranged at a distal tip of the otoscope, wherein at least one of the at least one source of radiation and/or the electronic imaging unit respectively is radially offset and/or an visual axis of the at least one source of radiation and/or of the electronic imaging unit respectively is tilted. Such an arrangement allows for capturing images of the eardrum and for illuminating the eardrum substantially irrespective of the relative position of a head portion of the otoscope within the ear canal. This allows for simplified/facilitated use by laypersons also.

According to one option, a plurality of sources of radiation or guides of radiation may be provided, especially at positions with maximum offset with respect to each other, e.g., with maximum radial offset. In particular, parallax radiation/illumination allows for acquiring and evaluating depth information. Instead of any source of radiation, at the distal tip, there may be guides of radiation only. In particular, any source of radiation, e.g., an LED, arranged at the tip may evoke thermal problems, limiting maximum lightning efficiency.

According to one embodiment of the invention, the electronic and/or optic means of the otoscope device are configured for calculating a ratio between at least two reflected spectral components or spectral ranges, especially by pixelwise division. In particular, calculating a ratio of reflected intensities may allow for cancelling out to a great extent any differences in illumination that are practically unavoidable. This ratio calculation may be done in order to achieve a "ratio image" that contains the relation of reflection ratios in a spatially resolved manner, especially for each pixel. Such a ratio image may be optimally suited for identifying and locating a structure like the eardrum.

According to one embodiment of the invention, the electronic and/or optic means of the otoscope device are configured for determining a ratio of radiation in the spectrum below 480 nm to 500 nm to radiation in the spectrum above 480 nm to 500 nm, especially the ratio of blue to red spectral components of reflected light, the electronic and/or optic means preferably configured for detecting or characterizing the eardrum depending on a specific minimum ratio.

According to one embodiment of the invention, the otoscope device further comprises at least two sources of radiation, namely at least one source of radiation emitting radiation in the spectrum below 500 nm, preferably below 480 nm, and at least one source of radiation emitting radiation in the spectrum above 480 nm or 500 nm, preferably above 580 nm or 630 nm, wherein the at least two sources of radiation are connected to the electronic and/or optic means, the electronic and/or optic means configured for determining a ratio of radiation in the spectrum below 480 nm to 500 nm to radiation in the spectrum above 480 nm to 500 nm, especially the ratio of blue to red spectral components of reflected light. Such a configuration allows for adjusting radiation parameters in a flexible manner, e.g., adjusting an intensity of illumination of specific spectral ranges independently. Such a configuration may ensure good accuracy of evaluation also. The source emitting radiation in the spectrum below 500 nm may provide an intensity of radiation which is higher (or which is adjusted to be higher) than in the spectrum above 580 nm emitted by the other source of radiation. The electronic and/or optic means may be configured for controlling each of the sources of radiation independently. In particular, the electronic and/or optic means may be configured for individually switching on or off or for dimming the respective source of radiation.

According to one embodiment of the invention, the electronic and/or optic means of the otoscope device are configured for evaluating a relative distribution or shift of ratios of radiation in the spectrum below 480 nm to 500 nm to radiation in the spectrum above 480 nm to 500 nm. The expression "distribution" may refer to a spatial resolution, and the expression "shift" may refer to a temporal or spatiotemporal resolution. Evaluating a relative distribution or shift allows for evaluating a relative degree of reddishness. The shift may be evaluated based on a threshold ratio, or based on previous ratios of previous measurements, especially in order to determine temporal mutations or changes, especially with respect to a medical trend or history. The electronic and/or optic means may comprise data storage means in order to store and compare data of any previous analysis.

According to one embodiment of the invention, the electronic and/or optic means are configured for evaluating a shift of a ratio of radiation in the spectrum below 480 nm to 500 nm to radiation in the spectrum above 480 nm to 500 nm, especially a shift of a ratio of blue to red, with respect to a shift of intensity of emitted and/or reflected radiation. Taking into account a ratio shift depending on an intensity shift allows for assessing the type of tissue more reliably. In particular, an amount or portion of hemoglobin may be evaluated, which allows for deducing the type or status of tissue.

According to one embodiment of the invention, an otoscope device is provided which comprises a radiation sensing unit configured for detecting radiation reflected by the patient's outer ear, especially by the eardrum, wherein the otoscope device further comprises: at least one or several sources of radiation, namely at least one source of radiation emitting radiation in the spectrum below 500 nm, preferably below 480 nm, and at least one source of radiation emitting radiation in the spectrum above 480 nm or 500 nm, and/or at least one source of radiation configured for electronic adjustment of the spectrum of emitted radiation; electronic and/or optic means connected to the source(s) of radiation and configured for determining spectral information of reflected radiation and configured for switching the source (s) of radiation and/or adjusting the spectrum of emitted radiation, the electronic and/or optic means configured for identifying and/or locating objects based on radiation in the spectrum below 480 nm to 500 nm, especially with respect to radiation in the spectrum above 480 nm to 500 nm. Such an otoscope allows for analyzing the ear canal based on a specific spectrum of emitted or reflected radiation, which may, e.g., allow to focus on the blue spectrum.

At least one of the above mentioned objectives is also attained by a method of identifying and/or locating objects in a subject's ear, especially by means of an otoscope device according to any of the preceding claims, comprising the steps:

(S1) providing an electronic imaging unit, especially by introducing the electronic imaging unit into an ear canal of a subject's outer ear;

(S2) capturing at least one image, especially a color image, of the patient's outer ear, especially of the eardrum, by means of the electronic imaging unit, especially based on reflected radiation of radiation emitted by at least one source of radiation;

(S3) determining spectral information, especially spatially resolved spectral information, to identify objects shown in the at least one image by electronic and/or optic means, especially by a logic unit, in order to automatically identify and/or locate at least one of the objects, especially the eardrum; and (S4) identifying and/or locating at least one of the objects, especially the eardrum, depending on a specific intensity of blue spectral components and/or UV spectral components, especially with respect to an amount of spectral components having wavelengths longer than 480 nm or 500 nm. Step S4 may be carried out depending on a spectral composition which exhibits a specific amount of specific spectral components, especially a specific amount of blue spectral components or spectral components having wavelengths shorter than 500 nm, preferably shorter than 480 nm. Such a method provides at least some of the advantages as described in context with the otoscope device. Identifying and/or locating objects may be carried out based on/depending on the spectral composition of the at least one image or a pixel or pixel area of the image.

According to one embodiment of the invention, the method further comprises the steps:

(S1a) introducing at least one source of radiation into the ear canal; and (S1b) illuminating the ear canal by means of the at least one source of radiation, especially by means of a light source, preferably an LED, which is configured for emitting blue light and/or light at longer wavelengths and/or by means of a source of radiation which is configured for emitting UV radiation, preferably with radiation having a spectral maximum in the spectrum of blue light. Illuminating the ear canal, especially with radiation having a specific spectral composition, may facilitate evaluation of spectral information.

According to one embodiment of the invention, spectral information is determined based on a ratio of wavelengths below 500 nm or 480 nm to wavelengths above 500 nm, 550 nm or 600 nm (especially the ratio of blue spectral components to red spectral components), wherein the ratio is evaluated, and wherein a high ratio (corresponding to a high amount of spectral components with wavelengths below 500 nm or 480 nm, especially a high amount of blue light) exceeding a threshold ratio is evaluated as an indicator for the eardrum, especially for a healthy eardrum. The ratio may refer to specific local area sections of an image or reflected radiation. The high ratio may be defined with respect to a specific threshold value which may be characteristic for a specific group of individuals, the high ratio exceeding the threshold ratio. Referring to such a ratio and evaluating the ratio may allow for determining the eardrum more reliably. According to one option, a ratio between two reflected spectral components is calculated, especially based on a ratio of reflected intensities. Often, differences in illumination are unavoidable within a complex structure like the ear canal. According to the present invention, differences in illumination may be cancelled out to a great extent. Ratio calculation may be done preferably pixel wise, achieving a "ratio image" that contains the relation of reflection ratios for each pixel, i.e., in a spatially resolved manner. Such a ratio image is optimally suited for identifying and locating a structure like the eardrum.

According to one embodiment of the invention, spectral information is determined based on brightness of the at least one image or a pixel or pixel area of the image, especially depending on a specific intensity of radiation of emitted and/or reflected radiation. Evaluating reflected radiation depending on a specific intensity of illumination may provide more accurate assessment of stray light components or light/radiation reflected by any tissue or liquid behind the eardrum.

According to one embodiment of the invention, the spectral information is determined in sections with respect to a specific pixel or pixel area of the at least one image. This allows for pattern recognition and accurate localization of objects within the image. In other words: Identifying and/or locating objects may comprise pattern recognition based on pixels or pixel areas of the at least one image which exhibit a certain ratio of spectral components and/or a minimum amount of specific spectral components and/or a specific spectral composition, in particular a minimum amount of blue spectral components (especially of blue light) and/or a specific spectral composition (e.g., specific spectral peaks) in the spectrum of wavelengths below 500 nm, especially between 380 nm and 480 nm or 500 nm. According to one variant, the spectral information is determined based on absolute ratio thresholds.

According to one embodiment of the invention, the method includes illuminating the ear canal, wherein an intensity of radiation is adjusted, especially reduced, to a minimum intensity for acquiring the at least one image, in order to reduce any stray radiations (especially reflected red light) to a minimum. Such a control step allows for more reliably assessing the origin of reflected radiation. Preferably, the electronic and/or optic means are configured to carry out such a control or intensity reduction. Preferably, the intensity of radiation is reduced in case the at least one image exceeds a specific amount of red spectral components, especially depending on a specific minimum ratio of blue spectral components to red spectral components.

According to one embodiment of the invention, an intensity of radiation is adjusted in case the at least one image exceeds a specific amount of spectral components having wavelengths longer than 550 nm, especially red spectral components, especially depending on a specific ratio of blue spectral components to red spectral components. Such an adjustment or control may reduce the amount of any stray light, e.g., light reflected from structures behind the eardrum.

According to one embodiment of the invention, determining spectral information comprises analysis of blue spectral components, wherein identifying and/or locating the at least one object comprises identifying and/or locating the eardrum and is carried out depending on the amount of blue spectral components, especially relative to the amount of red spectral components. Analyzing the amount of blue spectral components allows for focusing on the tissue properties of the eardrum, in order to better distinguish the eardrum from any surrounding tissue.

According to one embodiment of the invention, determining spectral information comprises pixelwise arithmetics, especially pixelwise division of intensities in the spectrum below 480 nm to 500 nm by intensities in the spectrum above 480 nm to 500 nm, e.g., of blue spectral intensities by red spectral intensities. Pixelwise analysis allows for determining pixelwise ratios. In particular, an intensity value of any pixel in the blue channel may be divided by an intensity value of the pixel in the green or red channel. This pixelwise calculation can be performed either with respect to color channels, e.g., demosaiced/demosaicing or debayering color channels, or preferably with respect to image data acquired by the image sensor, e.g., raw Bayer data. That calculation may provide a "ratio image" where each pixel value represents the blue to red (or green) ratio in the spatial region of the pixel. This method step allows for specifically analyzing spectral information which may indicate the eardrum or the position of the eardrum. In particular, pixelwise calculation may cancel out unavoidable illumination variances in the complex three-dimensional structure ear canal, exhibiting surfaces which are closer to the light source than others and therefore appear brighter than others.

According to one embodiment of the invention, the method further comprises a step of determining a condition, especially a medical condition, of the at least one object depending on a spectral composition which exhibits a specific minimum or maximum amount of specific spectral components, especially a specific amount of blue spectral components or a specific range of spectral component ratios. Preferably, step S5 is carried out based on threshold ratios, especially threshold ratios of blue to green and/or blue to red. Determining threshold values for specific spectral components or ratios thereof, especially blue and/or red components, allows for an easy method for automatically identifying specific objects, especially the eardrum. Any sophisticated, quite complicated algorithm (like, e.g., pattern recognition) is not necessarily required.

According to one embodiment of the invention, the eardrum is identified, wherein determining a condition comprises determining a healthy eardrum in case the spectral composition exhibits a specific amount of blue spectral components or a specific ratio range, preferably of ratios of blue to red. A specific amount of blue colors or UV spectral components or a specific ratio range may be evaluated as an indication for an eardrum which does not exhibit any widened capillaries.

According to one embodiment of the invention, the eardrum is located, wherein determining a condition comprises determining an pathologic eardrum in case the spectral composition exhibits a specific amount of blue spectral components, especially depending on or in relation to a specific amount of red spectral components or a specific ratio range, preferably of ratios of blue to red. A specific amount of blue colors or UV spectral components or a specific ratio range may be evaluated as an indication for an eardrum which exhibits widened capillaries or other typical signs/indications of inflammation.

According to one embodiment of the invention, the eardrum is identified or located, and wherein the method further comprises a step of providing an index to a user depending on the spectral composition of the at least one captured image, especially an inflammation index indicating a likelihood of inflammation of the eardrum, especially in case an amount of blue spectral components does not exceed a specific minimum amount or a specific ratio range, preferably of ratios of blue to red. In other words: If blue spectral components or a specific ratio range can only be identified to a relatively low degree, then, it is concluded that the likelihood of inflammation of the eardrum is high. Preferably, in the vicinity of an area characterized by a specific ratio range area typical for the eardrum, a predominantly red ratio range (a relatively low blue to red ratio) is evaluated as an indicator for inflammation.

According to one embodiment of the invention, the method further comprises calibrating the spectral range and/or the intensity of emitted radiation. Calibration, especially fixed calibrated color balance, may improve accuracy.

According to one embodiment of the invention, the method further comprises providing an inflammation index to a user, indicating a likelihood of inflammation of the eardrum, especially depending on a ratio of radiation in the spectrum below 480 nm to 500 nm to radiation in the spectrum above 480 nm to 500 nm which does not exceed a specific threshold ratio. The inflammation index may specifically refer to OME. OME is characterized by an effusion in the middle ear. It has been found that an effusion behind the transparent eardrum may be detected and evaluated based on a change in reflection spectra, especially due to mucus containing immune cells and cell debris. Under these conditions, the reflection spectra may shift away from the short wavelengths towards longer wavelengths, resulting, e.g., in a smaller/decreasing blue to red ratio.

According to one variant, the eardrum may be identified based on spectral information which is determined with respect to Rayleigh scattering. Rayleigh scattering may be evoked by molecular particles, which may be evaluated as an indicator for the eardrum. In contrast Mie scattering is typical for larger particles, e.g., cells. Evaluating/Acquiring spectral information with respect to the characteristics/particularities of Rayleigh scattering may improve accuracy of distinguishing the eardrum from other objects within the ear canal. Since Rayleigh scattering is wavelength-dependent it may be considered as an optical mechanism which may explain or constitute the finding that the eardrum reflects a higher degree of blue/UV spectral components than other objects within the ear canal.

At least one of the above mentioned objectives is also attained by a method of identifying and/or locating objects in a subject's ear, especially by means of an otoscope device according to any of the preceding claims, comprising the steps:

(S1) providing a radiation sensing unit, especially by introducing the radiation sensing unit into an ear canal of a subject's outer ear;

(S3) determining spectral information of reflected radiation by means of the radiation sensing unit, in order to automatically identify and/or locate at least one of the objects, especially the eardrum; and (S4) identifying and/or locating at least one of the objects, especially the eardrum, depending on a specific intensity of blue spectral components and/or UV spectral components within reflected radiation, especially with respect to an amount of spectral components having wavelengths longer than 480 nm or 500 nm. Such a method allows for analysing reflected radiation irrespective of any specific method of image acquisition and image processing. Analysis may be carried out directly with respect to reflected radiation. This method may provide a first result, e.g., in order to assess if there are any blue spectral components and/or UV spectral components at all. Also, this method may be carried out during insertion of an otoscope, in order to assess if the eardrum is (already) visible, or if the otoscope must be relocated. Once blue spectral components and/or UV spectral components are detected, image processing may be carried out, and analysis may be carried out with respect to specific pixels or pixel areas of the image.

At least one of the above mentioned objectives is also attained by a method of identifying and/or locating objects in a subject's ear, especially by means of an otoscope device according to any of the preceding device claims, comprising the steps:

(S3) determining spectral information of reflected radiation by means of the radiation sensing unit, in order to automatically identify and/or locate at least one of the objects, especially the eardrum; and (S4) identifying and/or locating at least one of the objects, especially the eardrum, depending on a specific intensity of blue spectral components and/or UV spectral components within reflected radiation, wherein identifying and/or locating is carried out based on a first spectral threshold value or with respect to a first range of wavelength. Preferably, the first spectral threshold value or a first range of wavelength defines at least one threshold value between blue and green light or between blue and red light. In particular, this method allows for identifying and/or locating the object based on a first ratio which is preferably a blue to green ratio. It has been found that based on a ratio which does not include/ consider red radiation at all, reliability of identifying/locating the eardrum may be increased, as most objects (tissue structures) within the ear canal include vessels and blood cells and reflect red light. In particular, it has been found that within the green spectrum the local concentration of hemoglobin has a reduced impact on reflectance. In other words: The ratio blue to green allows for squelching or reducing the impact of red reflections. In order to identify the eardrum, the ratio of blue to green may be even more signification or reliable than the ratio of blue to red. Identification may be carried out more reliably. Also, by referring to a ratio of blue to green, any intensity impact may be reduced. Therefore, in a first step, identification/localization may be carried out with respect to the ratio blue to green, and in a second step, analysing/characterizing the object/eardrum in more detail may be carried out with respect to the ratio blue to red. The ratio may refer to specific local area sections of an image or reflected radiation.

At least one of the above mentioned objectives is also attained by a method of identifying and/or locating and of characterizing objects in a subject's ear, especially by means of an otoscope device according to any of the preceding device claims, comprising the steps:

(S3) determining spectral information of reflected radiation by means of the radiation sensing unit, in order to automatically identify and/or locate at least one of the objects, especially the eardrum; and (S4) identifying and/or locating at least one of the objects, especially the eardrum, depending on a specific intensity of blue spectral components and/or UV spectral components within reflected radiation, wherein identifying and/or locating is carried out based on a second spectral threshold value or with respect to a second range of wavelength higher/longer than a first spectral threshold value or a first range of wavelength, or based on at least two different spectral threshold values or with respect to at least two different ranges of wavelength, the method comprising characterizing the object, especially medically characterizing the eardrum, based on the second spectral threshold value and/or the second range of wavelength, preferably with respect to specific surface area sections of the object. In particular, this method allows for analyzing the object based on a first ratio, e.g., blue to green, and characterizing the object based on a second ratio, e.g., blue to red. The ratio may refer to specific local area sections of an image or reflected radiation.

At least one of the above mentioned objectives is also attained by a method of identifying a healthy eardrum in a subject's ear, comprising the steps:

(S2) capturing at least one image of the eardrum by means of an electronic imaging unit, especially based on reflected radiation of radiation emitted by at least one source of radiation;

(S3) determining spectral information in order to automatically identify the eardrum shown in the at least one image by electronic and/or optic means, especially by a logic unit;

(S4) identifying and/or locating the eardrum depending on a specific intensity of blue spectral components and/or UV spectral components; and (S5a) determining the eardrum as being a healthy eardrum depending on a spectral composition which exhibits a specific amount of blue spectral components or spectral components having wavelengths shorter than 500 nm, preferably shorter than 480 nm, or a specific ration of spectral components. Such a method allows for automatically carrying out diagnosis, or at least pre-diagnosis. In particular, the method allows for providing a layperson with a risk index for a pathological ear condition. Subsequently a diagnosis may be carried out by a physician.

At least one of the above mentioned objectives is also attained by a method of identifying a healthy eardrum in a subject's ear, comprising the steps:

(S3) determining spectral information of reflected radiation, in order to automatically identify the eardrum based on reflected radiation;

(S4) identifying and/or locating the eardrum depending on a specific intensity of blue spectral components and/or UV spectral components within reflected radiation; and (S5a) determining the eardrum as being a healthy eardrum depending on a spectral composition which exhibits a specific amount of blue spectral components or spectral components having wavelengths shorter than 500 nm, preferably shorter than 480 nm, especially with respect to an amount of spectral components having wavelengths longer than 480 nm or 500 nm. Such a method allows for automatically carrying out diagnosis, or at least pre-diagnosis. In particular, the method allows laypersons, especially parents for assessing the risk that a person, especially a child, suffers OM. Subsequently a diagnosis may be carried out by a physician.

At least one of the above mentioned objectives is also attained by a method of identifying an inflamed eardrum in a subject's ear, comprising the steps:

(S2) capturing at least one image of the eardrum by means of an electronic imaging unit, especially based on reflected radiation of radiation emitted by at least one source of radiation;

(S3) determining spectral information in order to automatically identify the eardrum shown in the at least one image by electronic and/or optic means, especially by a logic unit;

(S4) identifying and/or locating the eardrum depending on a specific intensity of blue spectral components and/or UV spectral components; and (S5b) determining the eardrum as being inflamed depending on a spectral composition in the vicinity of the previously located eardrum area which exhibits a specific amount of red spectral components or spectral components having wavelengths longer than 480 nm to 500 nm and/or a specific amount of blue spectral components or spectral components having wavelengths shorter than 500 nm, preferably shorter than 480 nm, or a specific ratio of intensities at said wavelengths. Such a method allows for automatically carrying out diagnosis, or at least pre-diagnosis. In particular, the method allows for providing a layperson with a risk index for ear disease. Subsequently a diagnosis may be carried out by a physician.

At least one of the above mentioned objectives is also attained by a method of identifying an inflamed eardrum in a subject's ear, comprising the steps:

(S3) determining spectral information of reflected radiation, in order to automatically identify the eardrum based on reflected radiation;

(S4) identifying and/or locating the eardrum depending on a specific intensity of blue spectral components and/or UV spectral components within reflected radiation; and (S5b) determining the eardrum as being an inflamed eardrum depending on a spectral composition which exhibits a specific amount of red spectral components or spectral components having wavelengths longer than 480 nm to 500 nm and/or a specific amount of blue spectral components or spectral components having wavelengths shorter than 500 nm, preferably shorter than 480 nm, especially with respect to an amount of spectral components having wavelengths longer than 480 nm or 500 nm. As mentioned above, such a method allows for automatically carrying out diagnosis, or at least pre-diagnosis.

At least one of the above mentioned objectives is also attained by use of an otoscope, especially an otoscope according to the present invention, for determining spectral information, especially with respect to wavelengths shorter than 480 nm to 500 nm, and for identifying and/or locating objects based on reflected radiation or based on at least one image acquired by the otoscope, especially the eardrum, depending on a specific intensity of blue spectral components and/or UV spectral components.

At least one of the above mentioned objectives is also attained by use of electronic and/or optic means for determining spectral information, especially with respect to wavelengths shorter than 480 nm to 500 nm, and for identifying and/or locating objects, especially the eardrum, based on reflected radiation or based on at least one image acquired by an otoscope, especially an otoscope device according to the present invention, depending on a specific intensity of blue spectral components and/or UV spectral components.

At least one of the above mentioned objectives is also attained by use of an otoscope by manipulation by a layperson during its application for automatically and electronically determining spectral information with respect to wavelengths shorter than 480 nm to 500 nm for identifying and/or locating the eardrum based on reflected radiation or based on at least one image acquired by the otoscope depending on a specific intensity of blue spectral components and/or UV spectral components.

At least one of the above mentioned objectives is also attained by use of electronic and/or optic means and/or of an otoscope for automatically and electronically determining spectral information with respect to wavelengths shorter than 480 nm to 500 nm for medically characterizing the eardrum based on reflected radiation or based on at least one image acquired by the otoscope depending on a specific intensity of blue spectral components and/or UV spectral components.

BRIEF DESCRIPTION OF THE SEVERAL VIEWS OF THE DRAWINGS

In the following figures, the present invention is described by way of examples, wherein FIG. 1 schematically shows an otoscope device according to a first embodiment of the invention, wherein the otoscope device is introduced in an ear canal as far as a position from which the otoscope device is enabled to view the eardrum area ("look around the corner").

In case any reference sign is not explicitly described in a respective figure, it is referred to the other figures. In other words: Like reference characters refer to the same parts or the same type or group of device throughout the different views.

DETAILED DESCRIPTION

Figure 1:
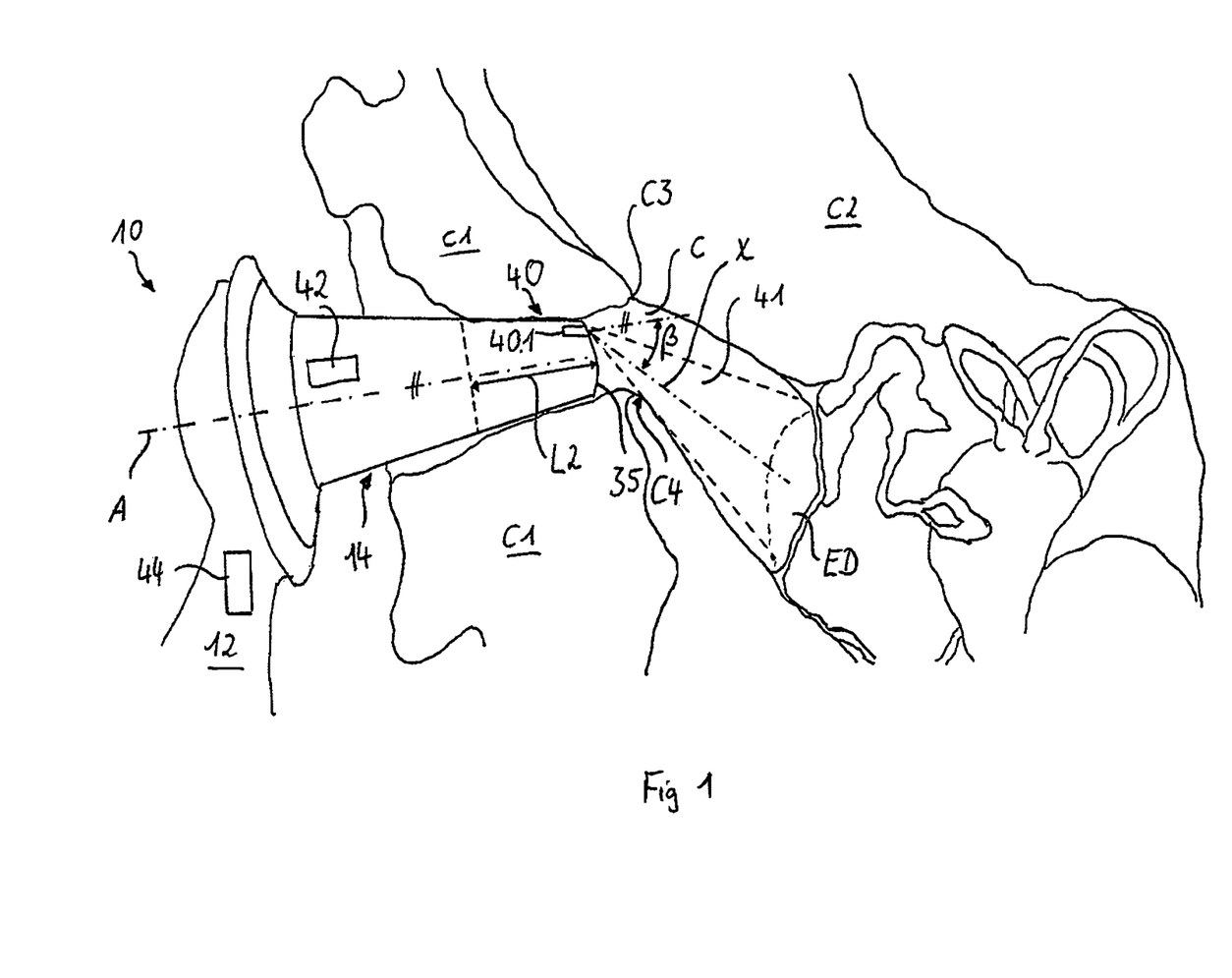

In FIG. 1, an otoscope 10 with a handle portion 12 and a head portion 14 including an electronic imaging unit 40 comprising a camera 40.1 is shown, wherein the camera 40.1 is positioned eccentrically (i.e., radially offset) with respect to a longitudinal axis A of the head portion 14. The camera 40.1 is positioned at a distal tip 35 of the head portion 14. The eccentricity (the radial offset) is, e.g., in the range of 1.5 mm to 2 mm. The head portion 14 is introduced into the ear canal C, and the outer surface of the head portion 14 or a probe cover (not shown) is in contact with soft connective tissue C1 surrounding the ear canal. In contrast to a hard bone section C2 of the ear canal, the soft connective tissue C1 is elastic and can be widened by the head portion 14. The camera 40.1 is in visual contact with the eardrum ED.

In a central section, the head portion 14 has a specific diameter, especially at an axial position defined by a specific length L2 which is preferably in the range of 28 mm to 32 mm, especially 20 mm. Along the length L2, the head portion 14 may exhibit a conical shape. The specific length L2 can be defined as the length along which the head portion 14 may be in contact with the patient's tissue, especially with the soft connective tissue C1 confining the outer ear canal, at least partially. The specific length L2 is preferably in the range of 18 mm to 22 mm, especially 20 mm. The diameter of the distal tip 35 is preferably in the range of 4.7 mm to 5.2 mm, more preferably 4.8 mm to 5 mm, especially 4.9 mm. A diameter at a middle portion of the head portion 14, especially at a distance of 20 mm from the distal tip 35, is preferably in the range of 8 mm to 9 mm, especially 8.5 mm.

The otoscope 10 is introduced within the ear canal C nearly as far as a curvature C4, i.e., nearly as far as a transition area C3 between the soft connective tissue C1 and the hard bone section C2. It is not required introducing the otoscope 10 any further/deeper. In the position shown in FIG. 1, the otoscope 10 is able to "look around the corner", in order to scan the eardrum ED. For this purpose, the camera 40.1 is arranged radially offset. The "corner" can be defined as the curvature C4 of the ear canal C.

The camera 40.1 has a field of vision 41 which is preferably conical. Geometrically, the field of vision 41 can be described as a conus with an opening angle in the range of at least 80°, preferably of at least 110°, e.g., 120°. The camera 40.1 preferably is a wide angle color video camera. An optical axis X of the camera 40.1 is arranged (tilted) at an angle β with respect to the longitudinal axis, allowing the device to "look around the corner" more effectively. The angle β preferably is in the range of 20° to 40°.

The otoscope 10 exhibits electronic and/or optic means 44 which are in communication with the camera 40.1, e.g., by wire or wireless. The electronic and/or optic means 44 may be arranged at/in the handle portion 12 and/or at/in the head portion 14. The electronic and/or optic means 44 are configured for determining spectral information or for spectral analysis of images (or pixels of a respective image, or specific image sections) captured by the camera 40.1. The electronic and/or optic means 44 may be connected to at least one source of radiation 42, especially a light source, which may be arranged at/in the handle portion 12 and/or at/in the head portion 14, and which may comprise a guide of radiation. In particular, the source of radiation 42 may be arranged at the distal tip of the head portion 14, at least partially. The source of radiation 42 may comprise at least one LED (especially an LED of cold white color or blue color) and also at least one light guide. The electronic and/or optic means 44 may be configured to control the source of radiation 42, especially to adjust an intensity of radiation/illumination.

Figure 2:
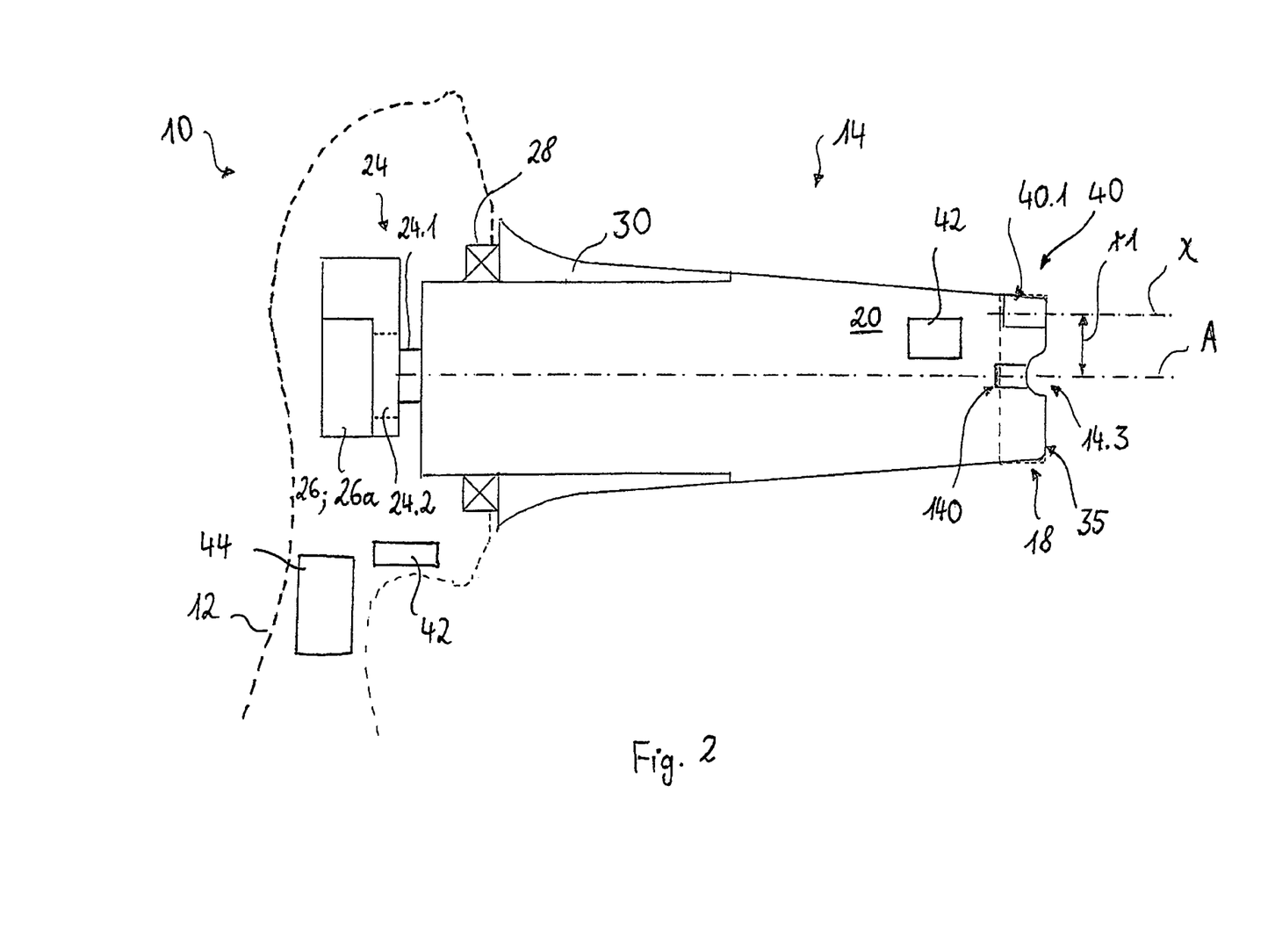
FIG. 2 schematically shows an otoscope device according to a second embodiment of the invention, wherein the otoscope device exhibits a plurality of technical features which facilitate its use, even by laypersons.

FIG. 2 shows an otoscope 10 with a handle portion 12 and a head portion 14. The head portion 14 has a distal end 18 including a distal tip 35, wherein the distal end 18 has a conical shape or a cylindrical shape (as indicated by the dashed line). An infrared sensor unit 140 is positioned centrically at the distal end 18. This position is only illustrated as an example. The distal end 18 may be provided with an indentation 14.3 for accommodating a reservoir portion of a probe cover (not shown). At the head portion 14, an electronic imaging unit 40 is provided, including a camera 40.1 having an optical axis X which is arranged radially offset with respect to a longitudinal axis A of the head portion 14, wherein the radial offset r1 of the optical axis X preferably is in a range between 1.5 mm and 2 mm. The camera 40.1 is arranged adjacent to an inner lateral surface of the distal end 18.

The otoscope 10 exhibits electronic and/or optic means 44, and may also exhibit at least one source of radiation 42 which may comprise a guide of radiation. In context with the electronic and/or optic means 44 and the source of radiation 42, it is referred to the description of FIG. 1.

In order to position the camera 40.1 in a favorable position for capturing an image of the eardrum, the head portion may further include a movable portion 20 and a support structure 30. The movable portion 20 can be rotated by a motion mechanism 24 which is arranged in the handle portion 12. The movable portion 20 can be rotated with respect to the support structure 30. The motion mechanism 24 includes a drive shaft 24.1 which connects the movable portion 20 with the handle portion 12. The motion mechanism 24 includes a motor 26, especially a brushless motor 26a, which is connected to the drive shaft 24.1. Optionally, a gear 24.2 may be provided between the motor 26a and the drive shaft 24.1. The movable portion 20 is supported by a bearing 28 which is supported by the handle portion 12. The support structure 30 is supported by the handle portion 12. The support structure 30 provides a portion of the outer lateral surface of the head portion 14. The support structure 30 is fixed at the handle portion 12 by means of the bearing 28.

The otoscope 10 shown in FIG. 2 allows for simplified application by laypersons. The camera 40.1 be positioned in a favorable eccentric position automatically, unit the camera is in visual contact with the eardrum. The otoscope 10 shown in FIG. 2 even allows for application by the same person whose ear has to be scanned (e.g., a person living alone). The otoscope 10 shown in FIG. 2 even allows for a first (pre-) diagnosis without any assistance. The technical features of the otoscope shown in FIG. 1 may be combined with the technical features of the otoscope shown in FIG. 2.

Figure 3:
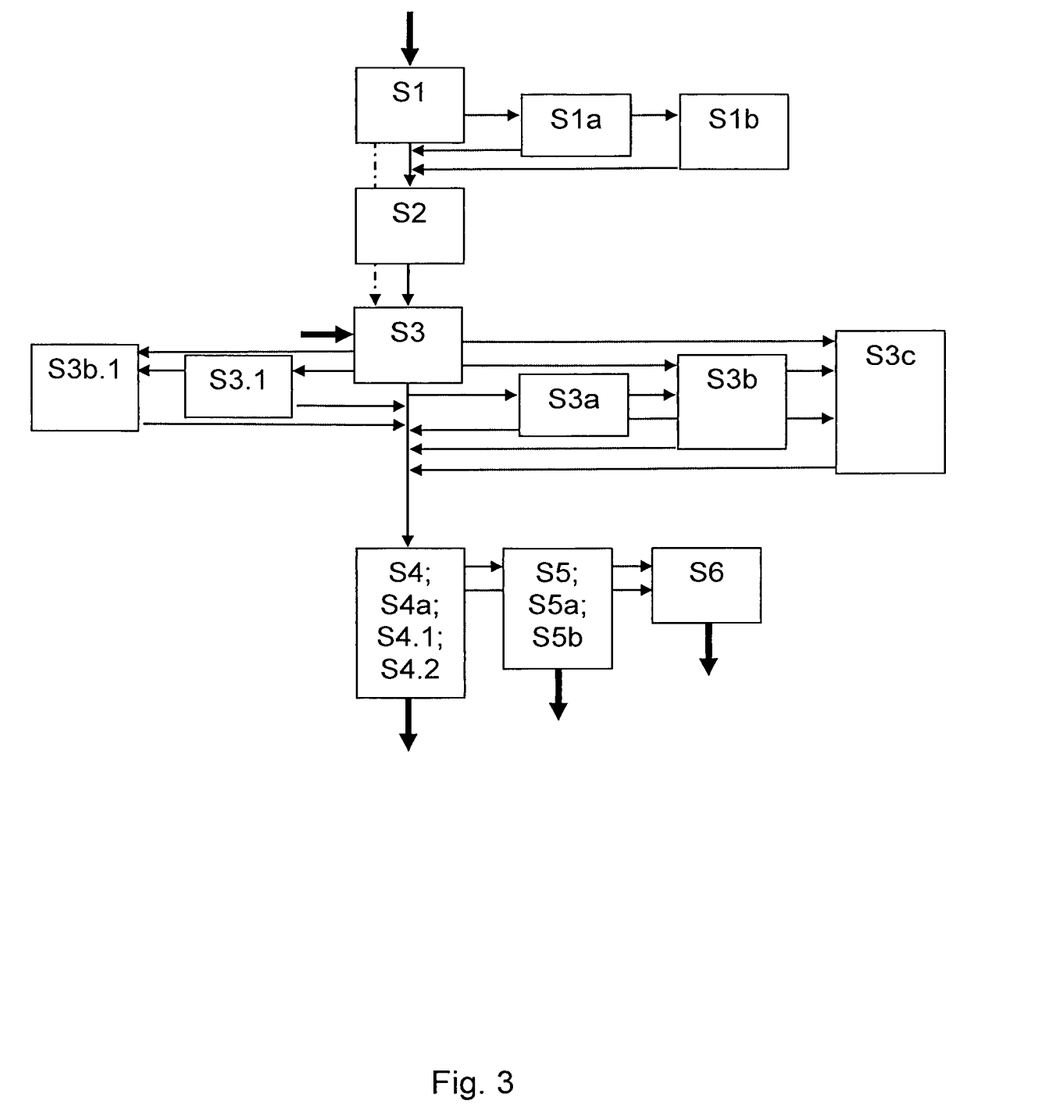
FIG. 3 schematically shows a flow chart of several methods of identifying and/or locating objects in a subject's ear according to embodiments of the present invention.

FIG. 3 shows a flow chart of examples of methods of identifying and/or locating objects. The respective method starts with a first step S1 of providing an electronic imaging unit, especially by introducing the electronic imaging unit into an ear canal of a subject's outer ear. In particular, the electronic imaging unit may comprise a camera which is arranged at a distal tip of a head portion of an otoscope. The step S1 may comprise a step S1a of introducing at least one source of radiation into the ear canal. Alternatively or in addition, the step S1 may comprise a step S1b of radiating, especially illuminating the ear canal. In a subsequent step S2, at least one image may be captured. In order to carry out spectral analysis, antecedent acquisition of an image is not necessarily required. Spectral analysis may be carried out directly on the basis of reflected radiation, as indicated by the dash-dotted line. In a step S3 subsequent to step S1 or S2, spectral information is determined, in order to identify and/or locate objects. Step S3 may be carried out directly after step S1. The step S3 may comprise a step S3a of determining spectral information based on a ratio of wavelengths (ratio of wavelengths of a specific range with respect to wavelengths of another specific range). Alternatively or in addition, the step S3 may comprise a step S3b of determining spectral information based on an intensity of radiation or based on brightness. Alternatively or in addition, the step S3 may comprise a step S3c of determining spectral information with respect to a specific image section. Step S3c may refer, e.g., to pixelwise spectral analysis. In particular, step S3c may be carried out in conjunction with steps S4.1 and/or S4.2. As indicated in FIG. 3, the steps S3a, S3b, S3c may be carried out independently from each other.

The step S3 may comprise a step S3.1 of calibrating the spectral range of emitted radiation. The step S3 may also comprise a step S3b.1 of calibrating the intensity of emitted radiation.

In a subsequent step S4, at least one object is identified and/or located, especially the eardrum, depending on a spectral composition which exhibits a specific amount of specific spectral components, especially a specific amount of blue spectral components. The step S4 may comprise a step S4a of providing information to a user indicating that the eardrum has been identified and/or that the otoscope has been placed/introduced correctly within the ear canal. In other words: Based on the analysis of spectral components, especially blue spectral components, the otoscope may automatically assess if the eardrum is visible, and if a layperson or physician has introduced the otoscope correctly. Therefore, the step S4a may allow for minimizing any risk of (accidental) misuse or any risk of misdiagnosis.

In a subsequent step S5, a condition, especially a medical condition, of the at least one object may be determined. In this step, a layperson may be provided with information which facilitates assessing any need of consulting/visiting a physician. In particular, it has been found that a spectral composition which differs from a specific spectral composition within the range of blue color or UV radiation may potentially indicate inflammation of the eardrum. An inflamed eardrum exhibits a reduced amount of blue tissue components, or does only reflect a reduced amount of blue or UV radiation, or does not reflect any blue or UV radiation at all. Determining the spectral composition of reflections of the eardrum may help the layperson to decide as to whether a physician should be visited or not. Any more advanced or final disease diagnosis may be carried out by the physician, e.g., on the basis of other symptoms exhibited by the subject, which are observed by the physician, or by the physician's further examination. Disease diagnosis may therefore not be derived from the output provided by embodiments of methods according to the invention. Acquired information is based on spectral analysis of the image and/or reflected radiation. Determining the degree/amount/ratio/percentage of blue spectral components, especially a specific amount of blue spectral components, may help the layperson to decide not to visit a physician. Nonetheless, step S4 and/or step S5 may not only assist a layperson, but also a physician. In other words: step S5 may allow for minimizing any risk of misdiagnosis and for providing a hint about an infection/inflammation risk.

Step S4 may comprise step S4.1 and/or step S4.2, namely a step S4.1 of identifying and/or locating the eardrum based on a first spectral threshold value or a first range of wavelength, and/or a step S4.2 of identifying and/or locating the eardrum based on a second spectral threshold value or a second range of wavelength or based on at least two different spectral threshold values or ranges of wavelength. Identification and/or localization based on at least one threshold value allows for carrying out the inventive method with respect to specific, examination objects or issues, e.g., with respect to more reliable distinction between the eardrum and further objects, or to the degree of reddishness of the eardrum. In particular, step S4.1 and/or S4.2 may be carried out in conjunction with step S3c, in order to determine specific surface area sections of the object, especially those sections which may be inflamed. Steps S3c and S4.1, S4.2 may provide specific pixels which represent/display an inflamed section of the eardrum. Steps S3c and S4.1, S4.2 may be carried out as an iterative method, especially between different points of time of analysis, in order to evaluate a progression of an inflammation or of other any disease patterns.

The step S5 may comprise a step S5a of determining a healthy eardrum in case the spectral composition exhibits a specific amount of blue spectral components, and/or a step S5b of determining an pathologic eardrum in case the spectral composition exhibits a specific amount of red spectral components and/or a specific amount of blue spectral components. The steps S5a and S5b may allow for further minimizing any risk of misdiagnosis, be it in context with use by a layperson or by a physician.

In a step S6 subsequent to step S4 or S5, a layperson may be provided with an index depending on the spectral composition of the at least one captured image, e.g., an inflammation index. An inflammation index may contain information about a healthy eardrum also. In particular, the inflammation index may be a low value (e.g., a value in the range of 1 to 3 of a scale from 1 to 10) in case there is a high amount of blue spectral components, especially in combination with a low amount of red spectral components.

The steps S3, S4, S5 and/or S6 may respectively be carried out by comparing the spectral information of the at least one image with spectral norm curves or with specific (predetermined) values of specific spectral components of the eardrum, respectively. Preferably, the spectral norm curves or specific (normalized) values refer to the UV spectrum and/or the spectrum of light, especially blue light.

Figure 4:
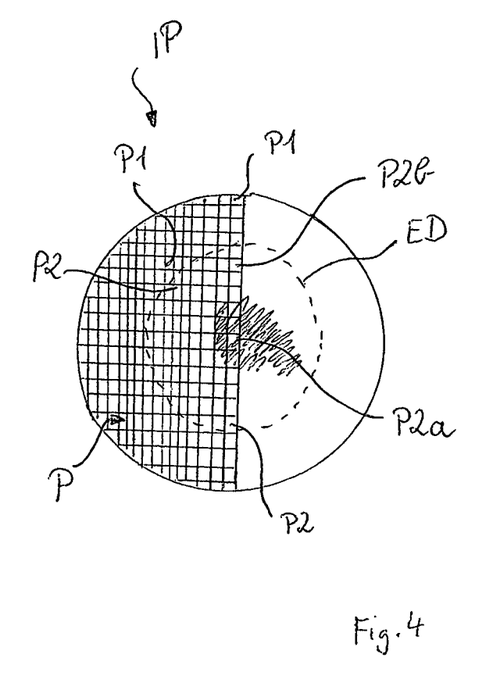
FIG. 4 schematically shows an acquired image composed of a plurality of pixels, wherein some of the pixels show a portion of the eardrum.

In FIG. 4, an acquired image IP composed of a plurality of pixels P is schematically shown. The image IP is composed of pixels P1 characterizing an object or part of the ear canal different than the eardrum, and pixels P2 characterizing the eardrum. The pixels P2 exhibit a ratio of spectral components in the spectrum below 480 nm to 500 nm to spectral components in the spectrum above 480 nm to 500 nm which is higher than the respective ratio of the pixels P1. The pixels P2 refer to both pixels P2a characterizing an inflamed part of the eardrum and pixels P2b characterizing a part of the eardrum which is not inflamed.

In particular, the respective ratio of the pixels P2a is higher than the ratio of pixels P1. In other words: Even in case the inflamed eardrum ED, the eardrum ED may be located and characterized based on the spectral ratio, especially a blue to green and/or blue to red ratio.

REFERENCE SIGNS 10 otoscope device
12 handle portion
14 head portion
14.3 indentation
18 distal end
24 motion mechanism
24.1 drive shaft
24.2 gear
26 motor
26a brushless motor
28 bearing
30 support structure
35 distal tip
40 electronic imaging unit, preferably an optoelectronic analysis unit
40.1 camera
41 field of vision
42 source of radiation, especially light source
44 electronic and/or optic means, especially logic unit
140 infrared sensor unit
A longitudinal axis
C ear canal
C1 soft tissue
C2 hard bone
C3 transition area
C4 curvature
ED ear drum
IP acquired image composed of a plurality of pixels
L2 specific length
P pixel
P1 pixel characterizing an object or part of the ear canal different from the eardrum
P2 pixel characterizing the eardrum
P2a pixel characterizing an inflamed part of the eardrum
P2b pixel characterizing a part of the eardrum which is not inflamed
r1 radial offset
X visual axis, especially optical axis
R tilt angle
S1 step of providing an electronic imaging unit
S1a step of introducing at least one source of radiation
S1b step of illuminating the ear canal
S2 step of capturing at least one image
S3 step of determining spectral information in order to identify and/or locate objects
S3.1 step of calibrating the spectral range of emitted radiation
S3a step of determining spectral information based on a ratio of wavelengths
S3b step of determining spectral information based on an intensity of radiation or based on brightness
S3b.1 step of calibrating the intensity of emitted radiation
S3c step of determining spectral information with respect to a specific image section
S4 step of identifying and/or locating at least one of the objects
S4.1 step of identifying and/or locating the eardrum based on a first spectral threshold value or a first range of wavelength
S4.2 step of identifying and/or locating the eardrum based on a second spectral threshold value or a second range of wavelength or based on at least two different spectral threshold values or ranges of wavelength
S4a step of providing information to a layperson indicating that the eardrum has been identified and/or that the otoscope has been placed/introduced correctly within the ear canal
S5 step of determining a condition, especially a medical condition, of the at least one object S5a step of determining a healthy eardrum in case the spectral composition exhibits a specific amount of blue spectral components S5b step of determining an pathologic eardrum in case the spectral composition exhibits a specific amount of red spectral components S6 step of providing an index to a layperson depending on the spectral composition of the at least one captured image

The invention claimed is:

1. An otoscope device configured to be manipulated and used by a layperson, comprising:
   a portion configured to be introduced in an ear canal of a patient's outer ear; and
   an electronic imaging unit configured for capturing at least one image of the patient's outer ear,
   wherein the otoscope device further comprises electronic and/or optic means comprising a logic unit or a processing unit, the electronic and/or optic means configured for determining spatially resolved spectral information by evaluating a ratio of reflected radiation in the spectrum below 480 nm to the reflected radiation in the spectrum above 480 nm, with respect to an intensity of emitted radiation, and configured for identifying and/or locating an eardrum shown in the at least one image and locating and identifying objects within the ear canal depending on the ratio.

2. The otoscope device according to claim 1, wherein the electronic and/or optic means are configured for determining spatially resolved spectral information with respect to specific sections of the patient's outer ear or of the at least one image.

3. The otoscope device according to claim 1, further comprising at least one source of radiation configured for illuminating the patient's outer ear at defined intensities in defined spectral bands.

4. The otoscope device according to claim 3, wherein the at least one source of radiation is configured for emitting blue light and/or UV radiation.

5. The otoscope device according to claim 3, wherein the electronic and/or optic means are configured for adjusting a spectral composition of radiation emitted by the at least one source of radiation.

6. The otoscope device according to claim 3, wherein the electronic and/or optic means are configured for calibration of a spectral composition of radiation emitted by the at least one source of radiation, and for comparing a determined spectral composition of reflected radiation with the calibrated spectral composition of emitted radiation.

7. The otoscope device according to claim 3, wherein the electronic and/or optic means are configured for adjusting the intensity of radiation of the at least one source of radiation, configured for reducing the intensity of radiation in case the at least one image exhibits a spectral composition which is outside a specific amount of spectral components having wavelengths longer than 480 nm, or blue spectral components to red spectral components falls below a specific minimum level or rises above a specific maximum level.

8. The otoscope device according to claim 1, comprising at least one combined or two or more separate sources of radiation, said sources of radiation emitting radiation in the spectrum below 480 nm, and said sources of radiation emitting radiation in the spectrum above 480 nm, wherein said sources of radiation are connected to the electronic and/or optic means.

9. The otoscope device according to claim 1, comprising at least one source of radiation, said at least one source of radiation being configured for emitting the entire visible light spectrum and/or UV radiation.

10. The otoscope device according to claim 1, wherein the electronic and/or optic means of the otoscope device are configured for evaluating the ratio or shift of ratios of radiation in the spectrum below 480 nm to radiation in the spectrum above 480 nm.

11. An otoscope device configured to be manipulated and used by a layperson, comprising:
    a radiation sensing unit configured for detecting radiation reflected by a patient's outer ear;
    wherein the otoscope device further comprises electronic and/or optic means comprising a logic unit or a processing unit, the electronic and/or optic means configured for determining spectral information of reflected radiation with respect to wavelengths shorter than 480 nm, configured for determining a ratio of radiation in the spectrum below 480 nm to radiation in the spectrum above 480 nm based on a specific intensity of reflected radiation within the spectrum of blue light and/or UV radiation, and configured for identifying and/or locating an eardrum of the patient and locating and identifying objects within an ear canal of the patient's outer ear depending on the determined ratio of radiation in the spectrum below 480 nm to radiation in the spectrum above 480 nm.

12. An otoscope device comprising a radiation sensing unit configured for detecting radiation reflected by a patient's outer ear;
    wherein the otoscope device further comprises:
    at least one source of radiation selected from the group consisting of a source of radiation emitting radiation in the spectrum below 480 nm, a source of radiation emitting radiation in the spectrum above 480 nm, and a source of radiation configured for electronic adjustment of the spectrum of emitted radiation; and
    electronic and/or optic means comprising a logic unit or a processing unit, connected to the at least one source of radiation and configured for determining spectral information of reflected radiation and configured for switching the at least one source of radiation and/or adjusting the spectrum of emitted radiation, the electronic and/or optic means configured for identifying and/or locating an eardrum of the patient and locating and identifying objects within an ear canal of the patient's outer ear by evaluating a ratio of reflected radiation in the spectrum below 480 nm to the reflected radiation in the spectrum above 480 nm, with respect to an intensity of the emitted radiation.

* * * * *